United States Patent [19]

Lilje

[11] Patent Number: 4,503,000

[45] Date of Patent: Mar. 5, 1985

[54] NUCLEOPHILIC SUBSTITUTION PROCESS

[75] Inventor: Kenneth C. Lilje, Baton Rouge, La.

[73] Assignee: Ethyl Corporation, Richmond, Va.

[21] Appl. No.: 487,039

[22] Filed: Apr. 21, 1983

[51] Int. Cl.³ ............................................ C07C 121/50
[52] U.S. Cl. ................................................. 260/465 G
[58] Field of Search .................................... 260/465 G

[56] References Cited

U.S. PATENT DOCUMENTS 4,370,278  1/1983  Stahly et al. ..................... 260/465 E

OTHER PUBLICATIONS

Golinski et al, Tetrahedron Letters, vol. 37, pp. 3495–3498, (1978).

Makosza et al., J. Org. Chem., vol. 45, pp. 1534–1535, (1980).

Makosza, Int. Conf. Chem. Biotechnol. Biol. Act. Nat. Prod. (Proc.), vol. 2, pp. 480–490, (1981).

Primary Examiner—Alan Siegel
Attorney, Agent, or Firm—Donald L. Johnson; John F. Sieberth; Patricia J. Hogan

[57] ABSTRACT

In a process for preparing a 2-(fluoronitrobenzene)acetonitrile by reacting a fluoronitrobenzene with an alpha,alpha-disubstituted acetonitrile in an inert solvent and in the presence of a base, the temperature is maintained not higher than about 15° C. to lead to the formation of a 2-(fluoro-2-nitrobenzene)acetonitrile. Preferred reactants are 2-fluoronitrobenzene and 2-chloropropionitrile, which lead to the formation of 2-(3-fluoro-2-nitrobenzene)propionitrile.

14 Claims, No Drawings

NUCLEOPHILIC SUBSTITUTION PROCESS

TECHNICAL FIELD

This invention relates to 2-(fluoronitrobenzene)acetonitriles and processes for preparing them.

BACKGROUND

As disclosed in U.S. Pat. No. 4,370,278 (Stahly et al.), it is known that 2-(fluoronitrobenzene)acetonitriles are useful for preparing flurbiprofen and related compounds and that the acetonitriles may be prepared by reacting a fluoronitrobenzene with an alpha-substituted alkyl cyanide in a substantially anhydrous aprotic solvent and in the presence of a base. Stahly et al. also teach that their reaction tends to be highly selective on the para positions of their fluoronitrobenzenes, and their Examples illustrate that selectivity.

There are pharmaceuticals and other materials which it is logical to believe could be formed from 2-(fluoronitrobenzene)acetonitriles having the acetonitrile substituent in a position ortho to the nitro substituent. It would therefore be desirable to find a way of modifying the Stahly et al. processes so as to make it possible to prepare such compounds.

SUMMARY OF INVENTION

An object of this invention is to provide novel processes for preparing 2-(fluoronitrobenzene)acetonitriles.

Another object is to provide such processes which lead to the formation of 2-(fluoro-2-nitrobenzene)acetonitriles.

Still another object is to provide novel 2-(fluoro-2-nitrobenzene)acetonitriles.

These and other objects are attained by using a temperature not higher than about 15° C. in a process for preparing a 2-(fluoronitrobenzene)acetonitrile by reacting a fluoronitrobenzene with an alpha,alpha-disubstituted acetonitrile in an inert solvent and in the presence of a base.

DETAILED DESCRIPTION

Fluoronitrobenzenes utilizable in the practice of the invention include the 2-, 3-, and 4-fluoronitrobenzenes. As a rule, 2-fluoronitrobenzene is preferred, although the fluoronitrobenzene that might be preferred in any given instance generally depends on the derivative that is desired as the ultimate product.

The alpha,alpha-disubstituted acetonitriles that can be used in the practice of the invention include a variety of such compounds, which—in general—may be represented by the formula:

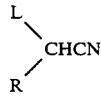

wherein L is a leaving group and R is a hydrocarbyl (e.g. alkyl, alkenyl, alkynyl, cycloalkyl, cycloalkenyl, aryl, aralkyl, etc.) or hydrocarbyloxyhydrocarbyl (e.g., alkoxyalkyl, aryloxyalkyl, alkoxyaryl, alkoxycycloalkyl, etc.) group which most preferably contains up to about 10 carbons.

Exemplary leaving groups, L, include halo, aryloxy, haloaryloxy, alkylthio, cycloalkylthio, arylthio, aralkylthio, haloalkylthio, halocycloalkylthio, haloarylthio, haloaralkylthio, or, less preferably, alkoxy, cycloalkoxy, aralkoxy, haloalkoxy, halocycloalkoxy, haloaralkoxy, and the like, as well as other suitable leaving groups which have been described in the literature, e.g., in Golinski et al., "'Vicarious' Nucleophilic Substitution of Hydrogen in Aromatic Nitro Compounds, *Tetrahedron Letters*, Vol. 37, pp. 3495–8 (1978); Makosza et al., "Vicarious Substitution of Hydrogen in Aromatic Nitro Compounds with Acetonitrile Derivatives," *Journal of Organic Chemistry*, Vol. 45, pp. 1534–5 (1980); and Makosza, "Some New Reactions of Carbanions. Vicarious Nucleophilic Substitution of Hydrogen in Nitroarenes," *Int. Conf. Chem. Biotechnol. Biol. Act. Nat. Prod. (Proc.)*, 1st, 1982, issue 2, pp. 480–490.

When the leaving group is an organic group, it is generally preferred that it contain not more than about 10 carbons, although organic leaving groups having an even higher carbon content are satisfactory in the practice of the invention. Preferably, the leaving group is halo, i.e., chloro, bromo, fluoro, or iodo; and it is more preferably chloro or bromo, most preferably chloro.

A few examples of alpha,alpha-disubstituted acetonitriles that can be used in the practice of the invention are 2-chloropropionitrile, 2-chlorobutyronitrile, 2-chlorovaleronitrile, 2-chlorocapronitrile, 2-chloro-4-pentenenitrile, 2-chloro-3,3-dimethylbutyronitrile, 2-chloro-2-phenylacetonitrile, 2-chloro-2-cyclohexylacetonitrile, 2-chloro-3-(3-chloro-o-tolyl)propionitrile, 2-chloro-3-phenylpropionitrile, the corresponding bromo and iodo compounds, and the like. The alpha-halopropionitriles, i.e., alpha-haloalkyl cyanides containing at least three carbons—particularly 2-chloropropionitrile and 2-bromopropionitrile—are especially preferred, although similar cyanides in which the alpha-halo substituent is replaced by one of the other leaving groups mentioned above are also highly desirable.

The solvent used in a fluoronitrobenzene/nitrile reaction of the invention may be any solvent that is inert under the conditions of the reaction, i.e., any solvent that will not prevent the reaction from occurring. Such solvents are substantially anhydrous and are generally aprotic, although solvents such as liquid ammonia are also utilizable.

Illustrative aprotic solvents which may be employed in the process of the invention include ethers such as diethyl ether, dibutyl ether, 1-ethoxyhexane, tetrahydrofuran, 1,4-dioxane, 1,3-dioxolane, diglyme, 1,2-diethoxyethane, anisole, etc.; tertiary amines such as pyridine, N-ethylpiperidine, triethyl amine, tributyl amine, N,N-diphenyl-N-methyl amine, N,N-dimethylaniline, etc.; dipolar aprotic solvents such as dimethyl sulfoxide, N,N-dimethylformamide, N,N-dimethylacetamide, dimethyl sulfone, tetramethylene sulfone, N-methylpyrrolidinone, etc.; and the like. However, the preferred solvents are solvents that are moderately polar, i.e., solvents having a dipole moment not higher than about 4.0 debyes, most preferably not higher than about 2.0 debyes, such as N,N-dimethylformamide, N,N-dimethylacetamide, N-methylpyrrolidinone, tetrahydrofuran, etc.

Bases useful in the practice of the invention include all bases strong enough to activate the nitrile reactant, e.g., alkaline earth metal compounds such as calcium oxide, calcium hydride, calcium hydroxide, barium oxide, barium hydroxide, magnesium hydroxide, zinc hydroxide, etc. However, the base is preferably an alkali metal compound, e.g., an organoalkali metal compound, alkali metal hydride, alkali metal hydroxide, alkali metal oxide, alkali metal amide, or alkali metal alcoholate, such as butyllithium, phenyllithium, ethylsodium, amylsodium, butylpotassium, benzylpotassium, sodium dimsylate (i.e., the sodium salt of diethysulfoxide), sodium hydride, potassium hydride, sodium hydroxide, potassium hydroxide, sodium oxide, potassium oxide, sodium amide, potassium amide, lithium diisopropylamide, sodium methoxide, potassium t-butoxide, the sodium salt of the monomethylether of ethylene glycol, sodium phenoxide, and the like. Ordinarily the use of an alkali metal hydroxide or alkoxide, such as sodium hydroxide, sodium t-butoxide, or potassium t-butoxide will be found most preferable.

Use of an alkali metal compound as the base permits the alternatives of using the alkali metal compound alone or in conjunction with a phase transfer catalyst, such as a quaternary ammonium salt, ethylene glycol, or a suitable crown ether. When a phase transfer catalyst is employed (1) the alkali metal compound may be any one of the alkali metal compounds generically or specifically indicated above, although the type of alkali metal compound being used determines the type of crown ether that is preferably utilized—lithium bases generally calling for the use of a 12-crown-4 ether, sodium bases generally calling for the use of a 15-crown-5 ether, and potassium bases generally calling for the use of an 18-crown-6 ether, and (2) the reaction medium may be any of the aprotic solvents mentioned above, or it may be an inert liquid hydrocarbon such as benzene, toluene, xylene, hexane, heptane, isooctane, or the like.

When an alkali metal hydride, especially a highly pure alkali metal hydride, is employed as the base, it is desirable to include a small amount of a transfer agent such as water, alcohol, or the like in the system. It is believed that the transfer agent activates the hydride by reacting therewith to form a small amount of the alkali metal hydroxide or alcoholate.

The process of the invention is conducted at a temperature not higher than about 15° C. to lead to the formation of 2-(fluoro-2-nitrobenzene)acetonitriles—the amount of ortho-isomer, i.e., 2-(fluoro-2-nitrobenzene)acetonitrile, formed in a given solvent generally increasing with a decrease in the temperature employed. There is no lower limit on the temperature that may be used other than the practical one, i.e., the freezing temperature of the solvent being utilized. Generally the temperature is in the range of about −20° to about 15°, preferably about −15° to about 5°, most preferably about −10° to about 0° C.

As in the process of Stahly et al., the fluoronitrobenzenacetonitrile synthesis of the invention appears to occur by a nucleophilic substitution mechanism whereby the nitrile undergoes a nucleophilic substitution on an unsubstituted ring carbon of the fluoronitrobenzene during which an alpha-substituent of the acetonitrile functions as a leaving group. It is conducted in a substantially anhydrous reaction system, and accordingly, except when a small amount of water (which is itself consumed by reaction with the alkali metal hydride) is employed as a transfer agent, the components of the reaction system should be brought together and maintained under a dry inert atmosphere. Thus, while it is possible to conduct the process in the presence of air, it is desirable to maintain the reaction system under an atmosphere of dry nitrogen or the like.

The fluoronitrobenzene and alpha,alpha-disubstituted acetonitrile may be used in amounts such as to provide a stoichiometric excess of either of the reactants or the stoichiometric amount of each. However, when a stoichiometric excess of the fluoronitrobenzene is employed, the quantity of product obtainable will be limited by the quantity of nitrile used, so it is desirable to utilize a stoichiometric excess of the nitrile. The amount of base employed is preferably such as to provide at least two molar equivalents of base per mol of fluoronitrobenzene, since the use of smaller amounts—although permitting the reaction to occur—makes the base the limiting reagent.

The mode of addition of the ingredients of the reaction system is not particularly critical. Accordingly, it is convenient to add the fluoronitrobenzene to a mixture of the other materials, add the base to a mixture of the other materials, add the reactants to a mixture of the base and inert solvent, introduce all four ingredients simultaneously into the reaction zone, or the like. Since the reaction ordinarily proceeds very rapidly, long reaction times are not required. The reaction will usually be completed within a matter of minutes or a few hours at the temperatures of the reaction.

When derivatives of the fluoronitrobenzeneacetonitriles are desired, they may be prepared by employing conventional techniques to convert to the desired derivatives the fluoronitrobenzeneacetonitriles made in accordance with the present invention.

As indicated above, the present invention is particularly advantageous in providing a readier and more economical route to the synthesis of pharmaceuticals and other chemical products that can be prepared from the novel 2-(fluoro-2-nitrobenzene)acetonitriles of the invention, most notably products such as compounds disclosed in U.S. Pat. Nos. 3,600,437, 4,126,635, and 4,182,774.

The following examples are given to illustrate the invention and are not intended as a limitation thereof.

EXAMPLE I

A suitable reaction vessel was charged with 25 ml of N,N-dimethylacetamide (DMAC), cooled to −10° C. under nitrogen, and then charged with 41.6 mmols of sodium t-butoxide. While the cold solution was stirred, a mixture of 22.3 mmols of 2-chloropropionitrile and 17.7 mmols of 2-fluoronitrobenzene in 1 ml of DMAC was added over a period of 10 minutes while maintaining the temperature at or below −5° C. The reaction mixture was stirred for an additional 35 minutes and then poured into 2.5 ml of concentrated HCl/ice. After warming, the suspension was extracted with aliquots of ether; and the ether phases were backwashed with water, dried, and evaporated to provide 3.32 g of a red oil. Analysis of the oil showed that the process resulted in a 53% yield of 2-(3-fluoro-4-nitrobenzene)propionitrile and a 22.7% yield of 2-(3-fluoro-2-nitrobenzene)propionitrile.

EXAMPLE II

A suitable reaction vessel was charged with 20 ml of DMAC, cooled to −10° C. under nitrogen, and then charged with 42.8 mmols of potassium t-butoxide, followed by a solution of 22.3 mmols of 2-chloropropionitrile and 17.7 mmols of 2-fluoronitrobenzene in 5 ml of DMAC. The addition took less than 10 minutes, during which the temperature was maintained at less than −5° C. with dry ice/isopropyl alcohol. The reaction mixture was stirred for an additional 30 minutes and then poured into 2.5 ml of concentrated HCl in ice. The suspension was extracted with aliquots of ether; and the combined ether phases were washed with water, dried, filtered, and evaporated to isolate the product. Analysis of the product by vpc showed 51 area % of 2-(3-fluoro-4-nitrobenzene)propionitrile and 20 area % of 2-(3-fluoro-2-nitrobenzene)propionitrile.

EXAMPLE III

A suitable reaction vessel was charged with 5 ml of N,N-dimethylformamide (DMF) and 5 ml of t-butanol under a stream of nitrogen and cooled to 10° C. Then 24.1 mmols of potassium t-butoxide were added, and the temperature was raised to 20° C. Cooling continued, the mixture solidified, and an additional 3 ml of DMF were added to increase fluidity. At a temperature of 10° C. a mixture of 8.9 mmols of 2-fluoronitrobenzene, 12.3 mmols of 2-chloropropionitrile, and 2 ml of DMF was added so as to keep the temperature in the range of 10°–15° C. The reaction mixture was then stirred at 5°–10° C. for 40 minutes and worked up as in Examples I and II to provide 1.65 g of a brown oil. Analysis of the oil by vpc showed 55 area % of 2-(3-fluoro-4-nitrobenzene)propionitrile and 17 area % of 2-(3-fluoro-2-nitrobenzene)propionitrile.

EXAMPLE IV

Following the same general procedure as in the previous examples, 24.6 mmols of 2-chloropropionitrile and 17.7 mmols of 2-fluoronitrobenzene were reacted in a DMF/t-butanol solvent mixture and in the presence of 48.9 mmols of sodium t-butoxide at a temperature of −10° C. After workup, 3.71 g of a dark oil were obtained, and vpc analysis showed that the process resulted in a 73% yield of 2-(3-fluoro-4-nitrobenzene)propionitrile and a 25% yield of 2-(3-fluoro-2-nitrobenzene)propionitrile.

EXAMPLE V

Following the same general procedure as in the previous examples, 22.3 mmols of 2-chloropropionitrile and 17.7 mmols of 2-fluoronitrobenzene were reacted in tetrahydrofuran in the presence of 42.5 mmols of potassium t-butoxide. The temperature was maintained in the range of −10° to 0° C. until the reactants had been added and at less than 0° C. during the subsequent reaction period. After workup, 3.7 g of a red-brown oil were obtained and subjected to vpc analysis, which showed a 10% yield of 2-(3-fluoro-4-nitrobenzene)propionitrile and a 20% yield of 2-(3-fluoro-2-nitrobenzene)propionitrile.

EXAMPLE VI

Following the same general procedure as in the previous examples, 22.3 mmols of 2-chloropropionitrile and 17.7 mmols of 2-fluoronitrobenzene were reacted in N-methylpyrrolidinone in the presence of 42.8 mmols of potassium t-butoxide. The temperature was maintained below −5° C. both during and after addition of the reactants. Analysis by vpc showed a yield of 57% of 2-(3-fluoro-4-nitrobenzene)propionitrile and a yield of 20% of 2-(3-fluoro-2-nitrobenzene)propionitrile.

It is obvious that many variations may be made in the products and processes set forth above without departing from the spirit and scope of this invention.

I claim:

1. In a process for preparing a 2-(fluoronitrobenzene)acetonitrile by reacting a fluoronitrobenzene with an alpha,alpha-disubstituted acetonitrile in an inert solvent and in the presence of a base, the improvement which comprises conducting the reaction at a temperature not higher than about 15° C. to form a 2-(fluoro-2-nitrobenzene)acetonitrile.

2. The process of claim 1 wherein the reaction is conducted at a temperature in the range of about −20° to 15° C.

3. The process of claim 2 wherein the reaction is conducted at a temperature in the range of about −15° to 5° C.

4. The process to claim 3 wherein the reaction is conducted at a temperature in the range of about −10° to 0° C.

5. The process of claim 1 wherein the fluoronitrobenzene is 2-fluoronitrobenzene.

6. The process of claim 1 wherein the alpha,alpha-disubstituted acetonitrile is an alpha-haloalkyl cyanide containing at least three carbons.

7. The process of claim 6 wherein the alpha,alpha-disubstituted acetontrile is alpha-chloropropionitrile.

8. The process of claim 1 wherein the solvent is an aprotic solvent having a dipole moment not higher than about 4.0 debyes.

9. The process of claim 8 wherein the solvent is an aprotic solvent having a dipole moment not higher than about 2.0 debyes.

10. The process of claim 1 wherein the base is an alkali metal compound.

11. The process of claim 10 wherein the base is an alkali metal hydroxide.

12. The process of claim 10 wherein the base is an alkali metal alkoxide.

13. The process of claim 1 wherein the fluoronitrobenzene is 2-fluoronitrobenzene, the alpha,alpha-disubstituted acetonitrile is alpha-chloropropionitrile, the inert solvent is an aprotic solvent having a dipole moment not higher than about 4.0 debyes, and the base is an alkali metal hydroxide or alkoxide.

14. The process of claim 13 wherein the inert solvent is an aprotic solvent having a dipole moment not higher than about 2.0 debyes.

* * * * *